United States Patent
Thompson

(10) Patent No.: US 7,662,018 B1
(45) Date of Patent: Feb. 16, 2010

(54) NURSING CUP

(76) Inventor: Pamela J. Thompson, 8703 S. 45th Ave., Omaha, NE (US) 68157

( * ) Notice: Subject to any disclaimer, the term of this patent is extended or adjusted under 35 U.S.C. 154(b) by 649 days.

(21) Appl. No.: 11/445,581

(22) Filed: Jun. 2, 2006

(51) Int. Cl.
*A41C 3/00* (2006.01)
(52) U.S. Cl. .............................. 450/37; 215/306; 604/74
(58) Field of Classification Search ............. 450/36–38; 215/306; 604/74, 76, 346
See application file for complete search history.

(56) References Cited

U.S. PATENT DOCUMENTS

| | | | | |
|---|---|---|---|---|
| 296,609 | A * | 4/1884 | Pattee | 604/346 |
| 2,044,913 | A * | 6/1936 | Miller | 473/610 |
| 3,840,012 | A * | 10/1974 | Rushton, Jr. | 604/346 |
| 4,270,538 | A * | 6/1981 | Murphy | 604/346 |
| 5,032,103 | A | 7/1991 | Larsson | 450/37 |
| 5,971,952 | A * | 10/1999 | Medo | 604/74 |
| 5,993,479 | A * | 11/1999 | Prentiss | 606/236 |
| 6,273,868 | B1 * | 8/2001 | Nordvik | 604/74 |
| 6,673,037 | B1 * | 1/2004 | Silver | 604/74 |
| 6,921,179 | B2 * | 7/2005 | Diak Ghanem | 362/84 |
| 7,351,251 | B2 * | 4/2008 | Garrett | 606/236 |
| 7,472,797 | B2 * | 1/2009 | Ostrowski | 215/306 |

* cited by examiner

*Primary Examiner*—Gloria Hale
(74) *Attorney, Agent, or Firm*—Holland & Hart LLP

(57) ABSTRACT

A nursing cup is provided with a cup-shaped base and a removable cap that define an open cavity between the two structures. An opening is formed through the cap to permit the passage of a nipple therethrough. Indicia is associated with the base and cap that may be selectively manipulated in a manner that indicates whether the container was used with a right breast or a left breast. One embodiment provides an external reservoir for the collection of breast milk. Another embodiment positions the opening in the cap between the peripheral edge and center portions of the cap in order to maximize volume within the device.

16 Claims, 6 Drawing Sheets

NURSING CUP

BACKGROUND

Women who nurse their babies frequently incur a myriad of different problems. Some problems include chafed, cracked or oversensitized nipples. Other problems involve the leakage of breast milk during and between nursing periods. Breast milk that leaks may stain overlying clothing, or worse, chafe the nipple, cause infection or assist in the growth of bacteria that may cause mastitis.

The prior art has provided numerous attempts at addressing these issues. Breast pads have been used for years to wick away breast milk from a leaking nipple and attempt to prevent the passage of the breast milk to overlying clothing. However, breast pads are disposable and can incur a considerable cost over time. Moreover, breast pads are only partially efficient at truly drawing moisture away from the nipple. More importantly, the breast milk absorbed by the breast pad is simply thrown away with the breast pad. This can amount to the waste of valuable breast milk that could be stored or used to top off a bottle of expressed breast milk. Furthermore, breast pads are placed directly against the nipple, which fails to address issues, such as chafed, cracked or overly sensitive nipples.

Another prior art device, disclosed within U.S. Pat. No. 3,840,012 teaches a two-piece breast shield. The shield is comprised of a hollow cup member that receives a lid, which is conformed to the shape of a woman's breast. An opening is disposed through the center of the shield, through which a nipple may be passed. The shield serves to collect milk that may leak from the nipple and further limits contact between overlaying clothing and the nipple. While such a device addresses a number of issues experienced by women, the device suffers from a number of shortcomings. First, a small port is provided in the bottom surface of the cup in order to allow milk to be poured from within. However, the small port is positioned in an area that would prevent the woman from placing the container on a horizontal surface for a few short moments while tending to her baby. If a woman were to lay the cup down, any expressed milk would simply pour from the port. Furthermore, the opening provided is far too small to provide any airflow around the nipple during use and releases only a small stream or several drops of milk at a time when the milk is being poured from within the cup.

Another prior art device disclosed within U.S. Pat. No. 5,032,103 teaches a breast shield that is also provided with a cup-shaped base. However, an elastic member is used as a lid for closing the base. An opening is formed through the center of the lid to permit passage of a nipple therethrough. The base is provided with a plurality of openings in order to permit proper ventilation of the nipple during use. However, while this solves a ventilation issue, it worsens the problem of preventing a user from simply laying the device down immediately after use. Furthermore, pouring expressed milk from the device can be a challenge due to the plurality of spaced-apart openings.

Such prior art devices suffer from additional shortcomings. First, none of the prior art devices provide any manner of recording whether the device was used on the woman's left or right breast. Breasts create a milk supply on the basic principal of supply and demand. It is important to stimulate and empty both breasts by nursing on both sides as equally as possible. Due to the frequency of feedings, and the late hours at which the feedings may take place, it is easy for anyone to forget which breast was used for nursing last. Various prior art methods and devices have been created to address this specific issue. For example, many woman may use stickers or safety pins with a brassiere cup in order to identify which breast was most recently used to feed their baby. Other prior art innovations have come in the form of somewhat complex nursing journals that must be completed, oftentimes in the dark, after each feeding. Other, more simple devices include bracelets that may be worn on the user's arm in order to designate the breast that was most recently used to feed the baby. However, such systems and methods are cumbersome, and are inconvenient for use during late night feedings in the dark. More importantly, they simply add to the methods and devices being employed, such as where a prior art breast shield is being used. Increasing the number of devices to be used or increasing the complexity which a woman must endure while nursing creates more problems than it solves.

Accordingly, what is needed is a novel system and method for collecting milk that is leaked from a breast during or between nursing sessions. Such a system and method should limit direct contact with the nipple area and provide a reasonable degree of air flow thereto. However, a truly useful system and method will increase the volume of milk that may be received by the system, make late night feedings easier, and provide a manner in which a woman may keep track of which breast was most recently used to nurse her baby.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A container is provided for receiving milk from a breast. The container is generally provided with a cup-shaped base, having at least one wall and a peripheral edge portion that define an open cavity. A cap is provided that is shaped and sized to operatively engage the peripheral edge portion of the base in a manner that generally encloses the open cavity. An opening is formed through the cap that is shaped and sized to accommodate at least a portion of a nipple on the breast. The cap and base are operatively coupled with one another in a manner that permits selective rotational movement of the cap and base with respect to one another. In one aspect of the invention, indicia is associated with the base and the cap that may be selectively manipulated in a manner that indicates whether the container was used with a right breast or a left breast.

The container may be provided with a spout that extends outwardly from either the base or the cap to provide, a reasonable level of airflow to the system and a means for pouring milk from therein. Another aspect of the invention provides the opening through the cap at a location that is between the peripheral edge and center portions of the cap in order to greatly increase the volume of breast milk that may be supported by the container. In another aspect, a reservoir is provided with an inner chamber that is in open fluid communication with the inner cavity of the base. The base and the reservoir may be shaped so that the base may be positioned between a brassiere cup and the woman's breast, while the reservoir is positioned outside of and beneath the brassiere cup. One or more of the various embodiments of the present invention may be comprised of a material that glows in the dark to provide ease of location during late night feedings.

It is therefore a principal object of the present invention to provide a nursing cup for collecting breast milk that leaks from a woman's breast during or between nursing periods.

A further object of the present invention is to provide a nursing cup that assists a nursing woman who is experiencing problems relating to nipple chafing, cracking, inversion or oversensitivity.

Still another object of the present invention is to provide a nursing cup for collecting breast milk that receives a woman's nipple at a location that maximizes the amount of breast milk that may be collected.

Yet another object of the present invention is to provide a nursing cup for collecting breast milk that is provided with an external reservoir for maximizing the volume of breast milk that may be collected.

A further object of the present invention is to provide a nursing cup for collecting breast milk that leaks from a woman's nipple during and between nursing periods that easily denotes which breast was last used for nursing.

Still another object of the present invention is to provide a nursing cup for collecting milk that leaks from a woman's breast during or between nursing periods that is comprised of a material that glows in the dark so that the device may be easily located and used during late night feedings.

Yet another object of the present invention is to provide a nursing cup for use in collecting breast milk that leaks from a woman's breast that is relatively simple to manufacture and use.

These and other objects of the present invention will be apparent after consideration of the Detailed Description and Figures herein.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Figure 1:
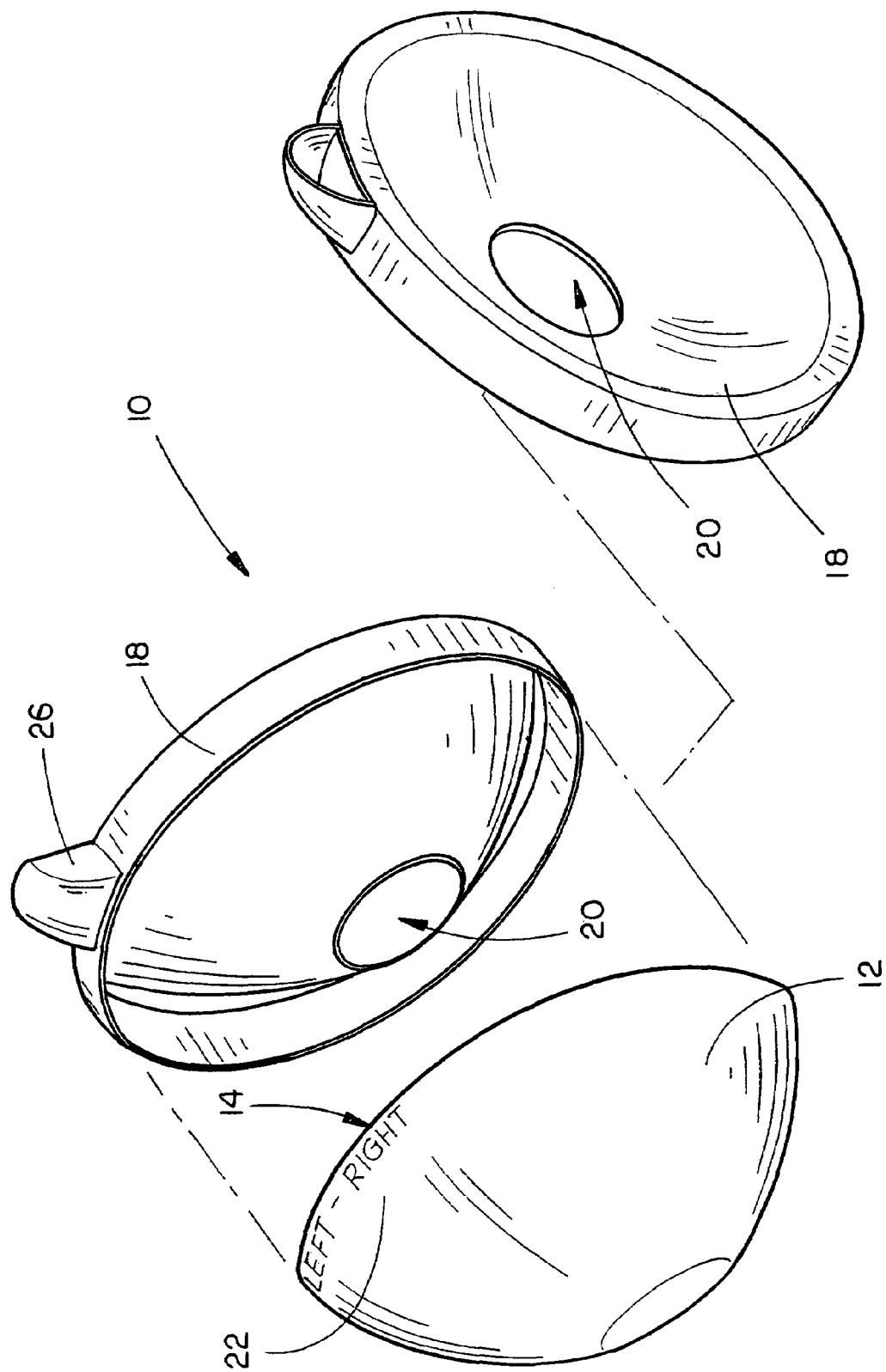
FIG. 1 depicts a partially exploded, perspective view of one embodiment of the nursing cup.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The nursing cup 10 is provided with a generally cup-shaped base 12 that may be formed from one or more walls that terminate at a peripheral edge portion 14 to define an open cavity 16. A cap 18 is provided with a shape and size to be operatively engaged with the peripheral edge portion 14 of the base 12 in order to at least partially enclose the open cavity 16. An opening 20 is formed through the cap 18 and is shaped and sized to accommodate at least a portion of a nipple on the user's breast It is contemplated that the base 12 and the cap 18 may be coupled to one another in many different manners that substantially prevent the passage of fluid between the two structures. Simple snap-fit or friction-fit designs may be preferred. In one preferred embodiment, however, the base 12 and cap 18 should be coupled with one another in a manner that permits selective rotational movement between the base 12 and the cap 18 for reasons that will be described in detail herein below.

Indicia 22 should be associated with either or both of the base 12 and cap 18 that may be selectively manipulated in a manner that indicates whether the nursing cup 10 was last used, or should next be used, with a right breast or a left breast. In one embodiment, depicted in FIG. 1, the indicia 22 uses the words "Right" and "Left". However, it is contemplated that other indicia, such as "R" and "L" and the like could be used as well. In one embodiment, the indicia 22 are positioned on the cap 18 and an indicator 24, which may be a line, dot, groove, or even a pour spout 26, may be positioned on the base 12 so that the base 12 and cap 18 may be selectively rotated with respect to one another to associate the indicator 24 with the "Right" or "Left" portions of the indicia 22. Likewise, it is contemplated that the indicia 22 could be positioned on the base 12 and an indicator could be positioned on the cap 18.

Figure 2:
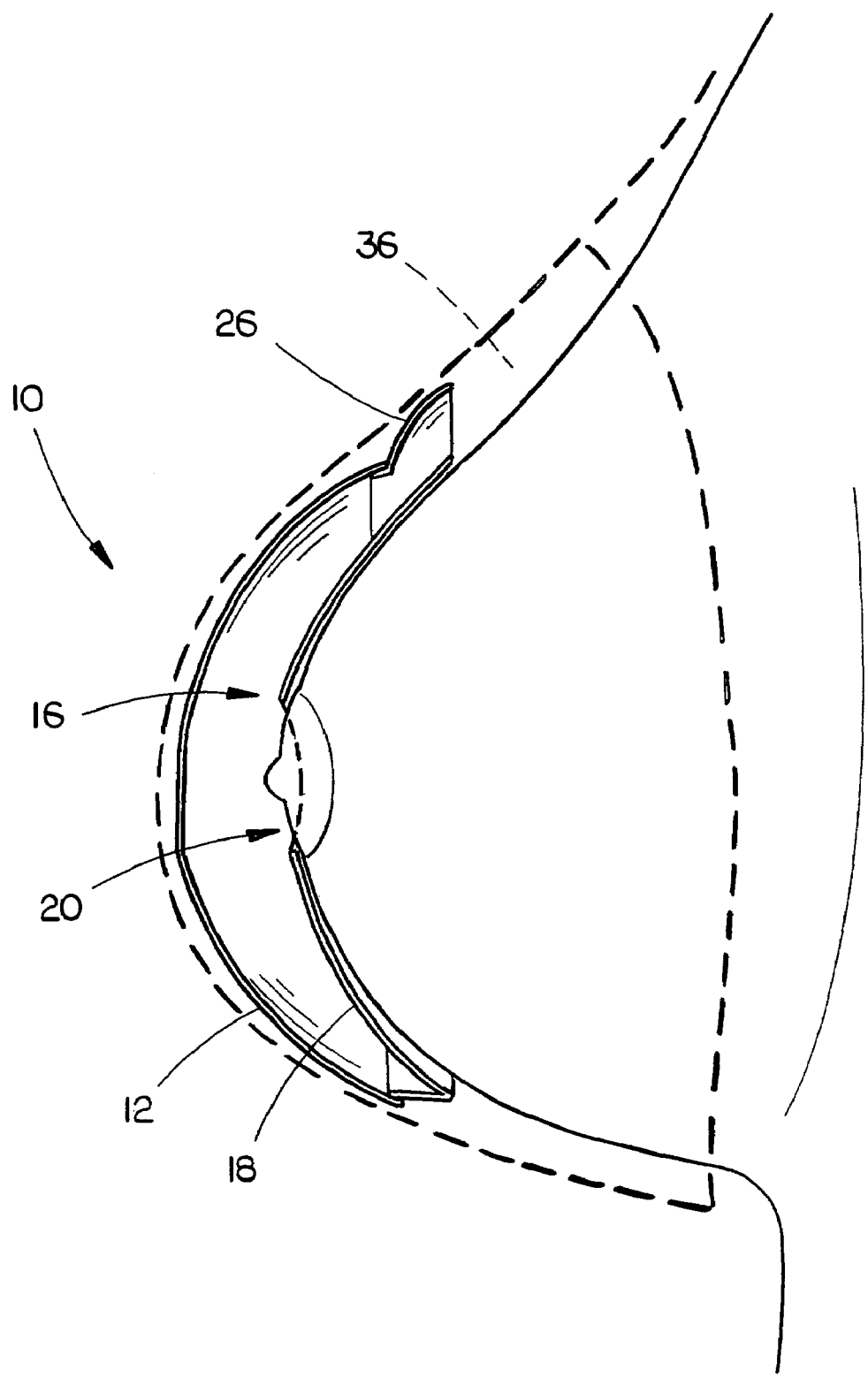
FIG. 2 depicts a cut-away, side elevation view of the nursing cup depicted in FIG. 1 as it may be positioned intermediate a brassiere cup and a breast.
Figure 3:
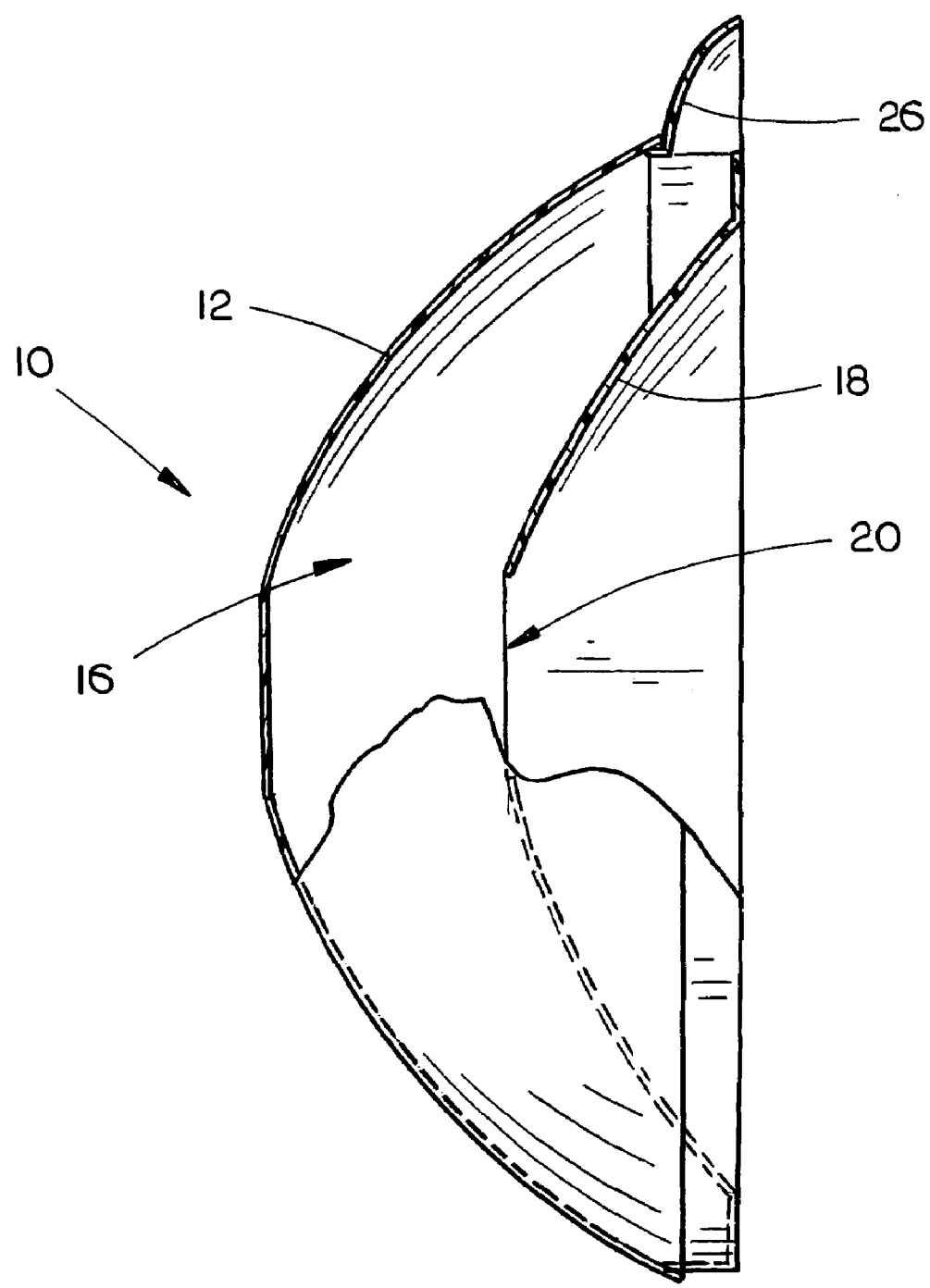
FIG. 3 depicts a cut-away, side elevation view of another embodiment of the nursing cup.
Figure 4:
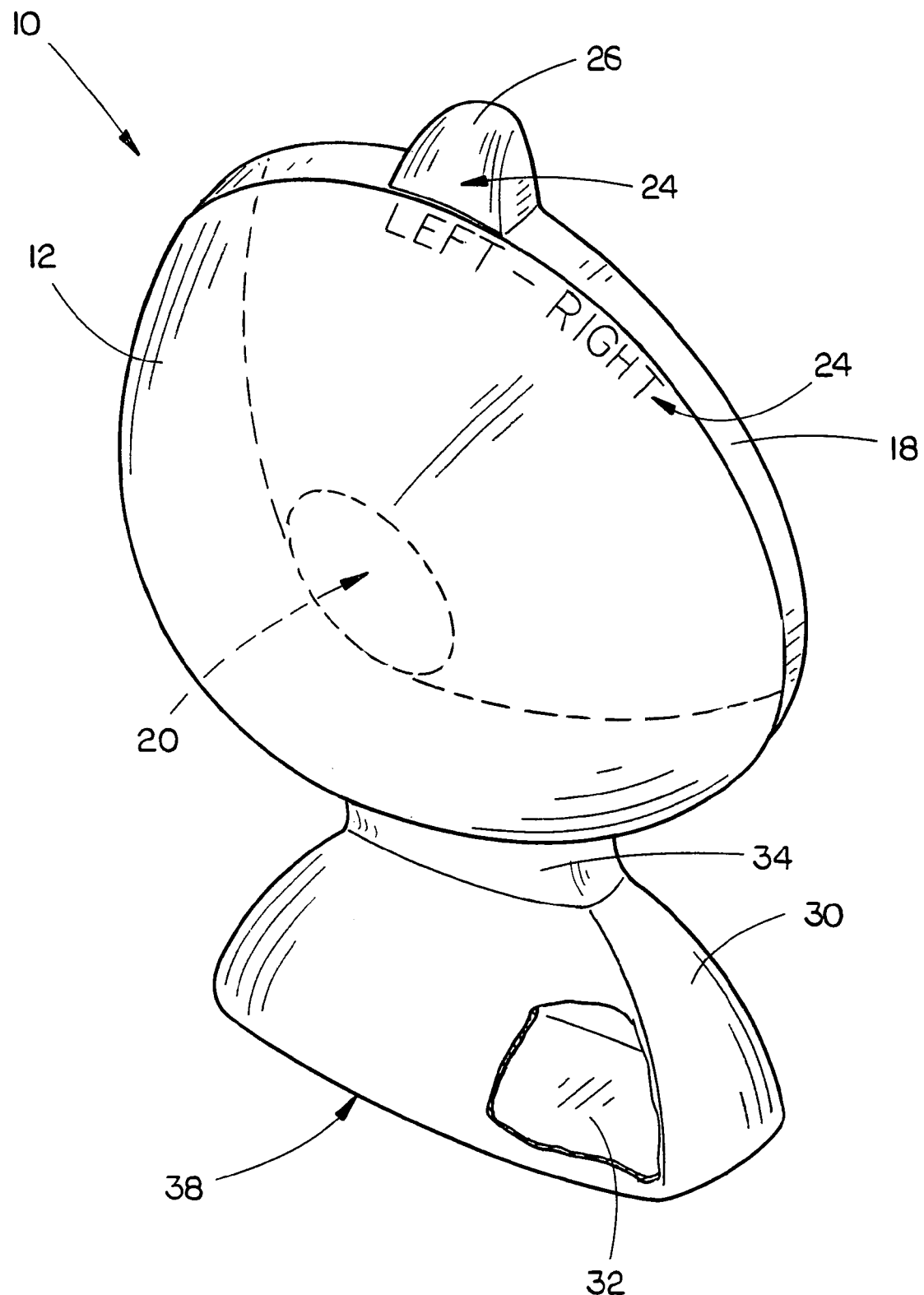
FIG. 4 depicts a rear perspective view of still another embodiment of the nursing cup.

The pour spout 26 may be provided to serve several other purposes other than to be an indicator 24. For example, the pour spout should be provided in open fluid communication with the open cavity 16 of the base 12. In this manner, the pour spout 26 will provide a convenient manner for emptying breast milk collected within the nursing cup 10. To the extent that the nursing cup 10 is designed to have an upper portion and a lower portion when the breast cup is being used, such as depicted in FIG. 2, the pour spout 26 will preferably be located in the upper end portion. While various sizes and configurations of pour spouts 26 are contemplated, the pour spout should provide a relatively large opening to enable the contents of the nursing cup 10 to be emptied quickly and easily. Moreover, a relatively large pour spout 26 will accommodate the flow of air in and out of the nursing cup 10. As design considerations dictate, the pour spout 26 may be provided to extend outwardly from either the base 12 or the cap 18. It is further contemplated that the pour spout 26 may be provided in multiple components that may be distributed across both the base 12 and cap 18. Regardless of its location, however, the pour spout 26 will provide a convenient structure that may be engaged by a user when the base 12 and cap 18 are moved with respect to one another. This will provide an increased level of ease, especially when the user's hands may be wet.

Figure 8:
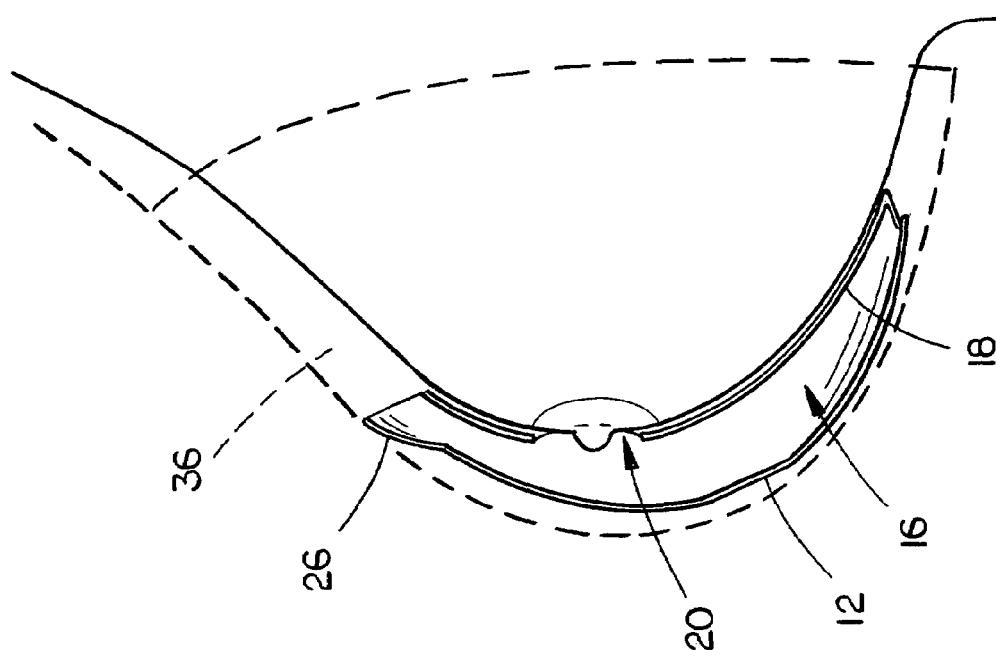
FIG. 8 depicts a cut-away, side elevation view of the nursing cup depicted in FIG. 7 as it may be positioned intermediate a brassiere cup and a breast.
Figure 7:
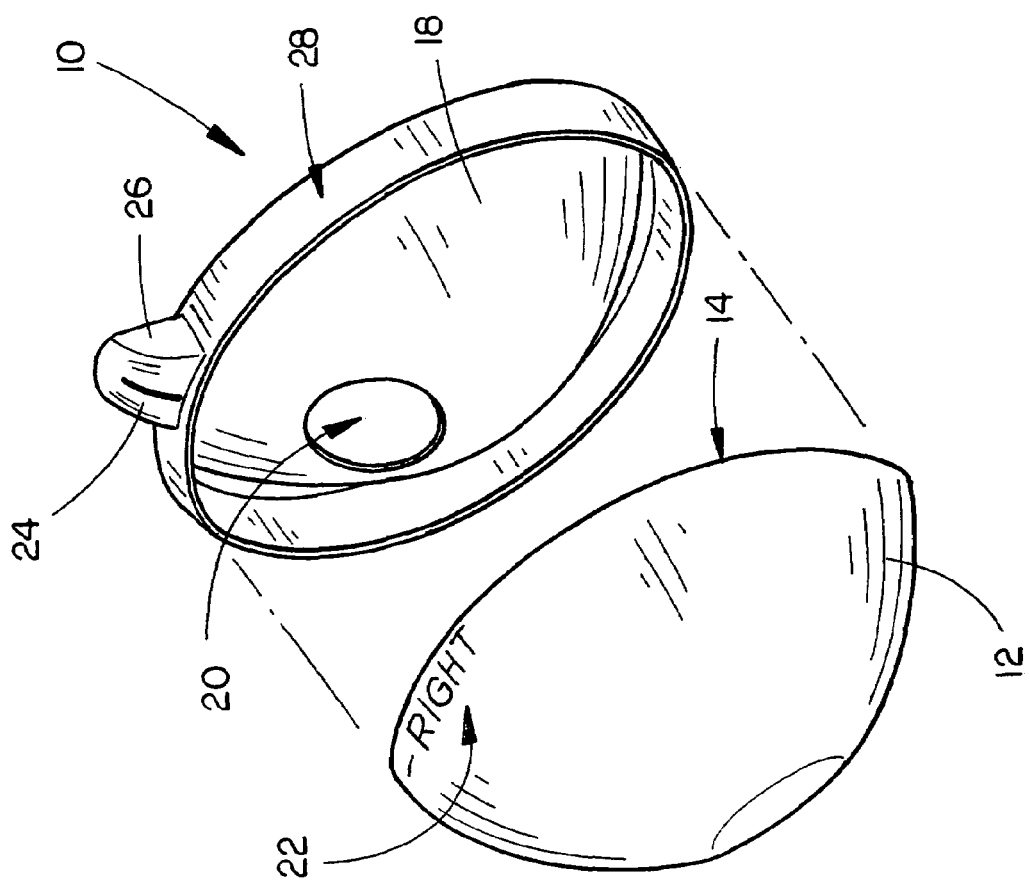
FIG. 7 depicts a rear perspective view of yet another embodiment of the nursing cup.

In one embodiment, where a relatively large available volume within the nursing cup 10 is desired, an axis extending perpendicularly through a central portion of the opening 20 is positioned between a peripheral edge portion 28 and an axis extending perpendicularly through a central portion of the cap 18. An example of such an embodiment is depicted in FIGS. 7 and 8. As can be seen, the opening 20 is simply moved toward the upper end portion of the nursing cup 10, creating a greater volume in the lower end portion. It is contemplated that such a design will position the nursing cup 10 in a slightly lower position within the user's brassiere cup, as depicted in FIG. 8.

Figure 6:
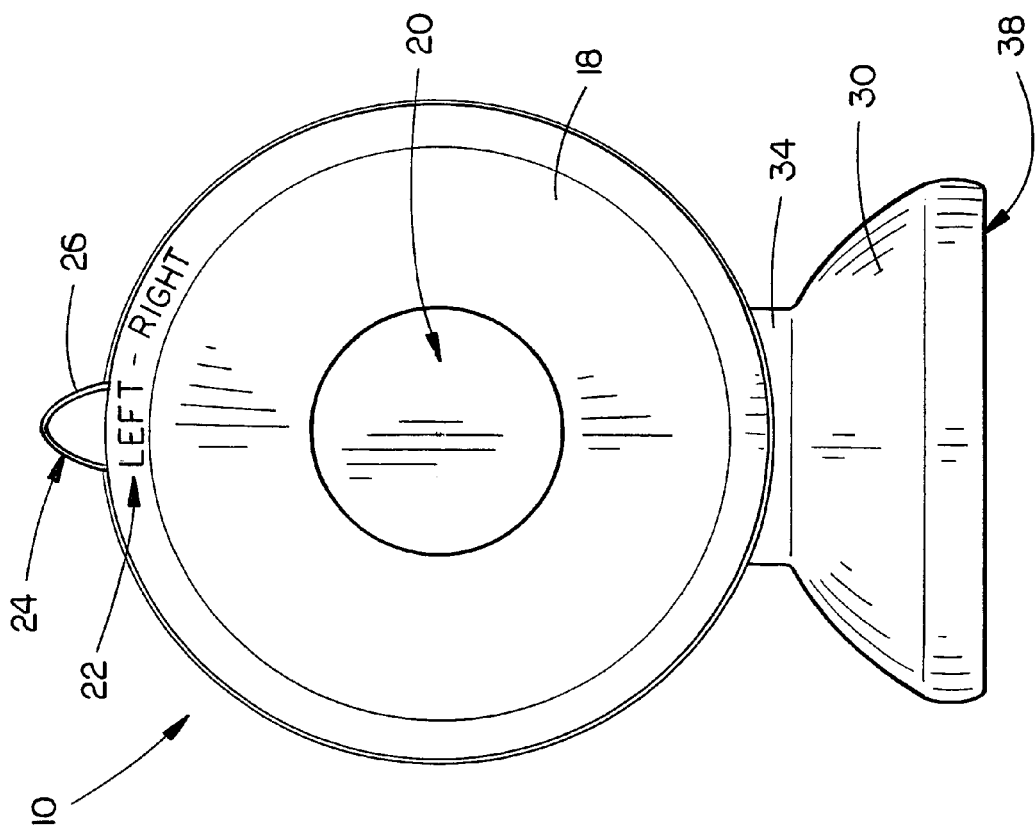
FIG. 6 depicts a front elevation view of the nursing cup depicted in FIG. 4.
Figure 5:
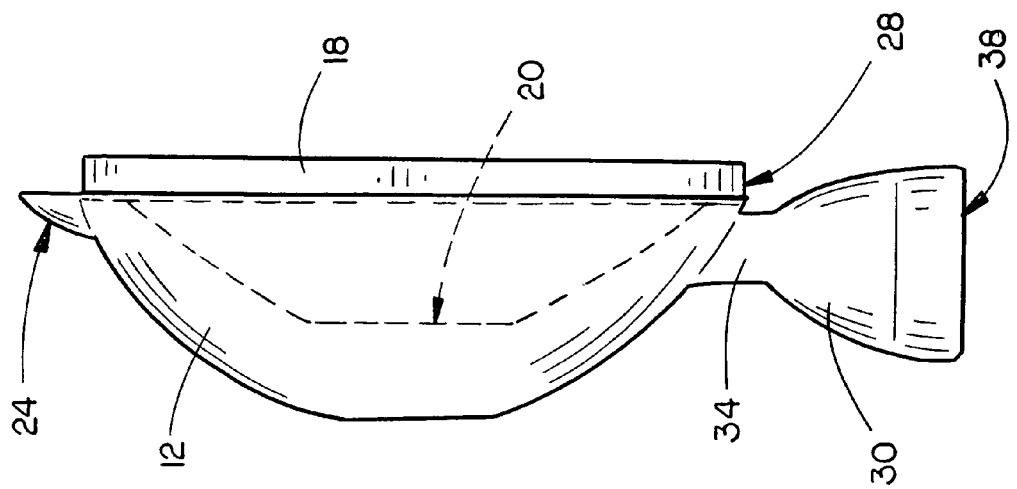
FIG. 5 depicts a side elevation view of the nursing cup depicted in FIG. 4.

In another embodiment, a reservoir 30 may be positioned adjacent the base 12 and provided with an inner chamber 32 that is in open fluid communication with the open cavity 16 of the base 12. In one preferred embodiment, an open neck member 34 connects the reservoir 30 with the base 12. It may be desirable to form the neck member 34 with a cross-sectional height that is shorter than a cross-sectional height of the base 12 or the reservoir 30. Moreover, the base 12 and neck member 34 should be shaped relative to one another so that the base 12 may be substantially disposed within a cup 36 of a brassiere, while the brassiere is worn by an individual, thus disposing the neck member 34 between a peripheral edge portion of the brassiere cup 36 and supporting the reservoir 30 outside the brassiere cup 36 in a manner that permits fluid to drain freely from the base 12 into the reservoir 30. It may be desirable in such a structural design to provide the neck member 34 with a flexible nature, so that the base 12 and reservoir 30 may be selectively moved with respect to one another. This will be of benefit when the nursing cup 10 is worn by an individual who may bend forward or move in a nature that would possibly push the reservoir 30 inward toward the user's abdomen. Therefore, a resiliently deformable material may be preferred so that the neck member 34 will return the base 12 and reservoir 30 to their original relative positions. It may be desirable to provide the reservoir with a lower end portion 38 that is shaped to permit the nursing cup 10 to be positioned on the lower end portion 38 and support the base 12 above an operating surface, as depicted in FIGS. 5 and 6. This will allow the user to easily set the nursing cup 10 on a table or other horizontal surface with the breast milk safely contained within the reservoir 30. To that end, it may also be desirable to shape and position a reverse surface of the reservoir 30, relative to a reverse surface of the base 12 so that the nursing cup 10 may also be laid against a horizontal surface on its back. In this position, the base 12 and/or reservoir 30 may safely contain the breast milk without fear of spilling the same.

It is contemplated that the nursing cup 10 may be formed from nearly any material, however, various polymers will provide ease of manufacture at low costs. It is further contemplated that the nursing cup 10, or portions thereof, could be comprised of one or more materials containing phosphors so that at least portions of the nursing cup 10 will radiate visible light after the phosphors are energized. More specifically, the material could be exposed to light so that, during a later feeding at night, the nursing cup 10, or at least a portion thereof, would glow in the dark. This will enable the user to easily locate the nursing cup 10. More specifically, the indicia 22 and the indicator 24 may be comprised of such material to further aid the user in identifying whether the container was last used with a right breast or a left breast.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

What is claimed is:

1. A container for receiving milk from a breast, the container comprising:

a cup-shaped base, having at least one wall and a peripheral edge portion that define an open cavity;

a cap that is shaped and sized to operatively engage the peripheral edge portion of said base in a manner that at least partially encloses said open cavity; said cap having an opening that is shaped and sized to accommodate at least a portion of a nipple on the breast; said cap and said base being operatively coupled with one another in a manner that permits selective rotational movement of said cap and said base with respect to one another; and indicia, associated with both said base and said cap, that may be selectively manipulated in a manner that indicates whether the container was used with a right breast or a left breast; said indicia comprising a first indicia that denotes "right" and a second indicia that denotes "left"; the first and second indicia being positioned on said cap and an indicator being positioned on said base so that said base and said cap may be selectively rotated with respect to one another to associate said indicator with one of said first or second indicia.

2. The container of claim 1 wherein said indicator is provided in the form of a spout that extends outwardly from said base; said spout having an opening that is in open fluid communication with the open cavity of said base.

3. The container of claim 1 wherein the first and second indicia are positioned on said base and an indicator is positioned on said cap so that said base and said cap may be selectively rotated with respect to one another to associate said indicator with one of said first or second indicia.

4. The container of claim 3 wherein said indicator is provided in the form of a spout that extends outwardly from a peripheral edge portion of said cap; said spout having an opening that is in open fluid communication with the open cavity of said base when said cap and said base are coupled with one another.

5. A container for receiving milk from a breast, the container comprising:

a cup-shaped base, having at least one wall and a peripheral edge portion that define an open cavity;

a cap that is shaped and sized to operatively engage the peripheral edge portion of said base in a manner that at least partially encloses said open cavity; said cap having an opening that is shaped and sized to accommodate at least a portion of a nipple on the breast; said cap and said base being operatively coupled with one another in a manner that permits selective rotational movement of said cap and said base with respect to one another;

indicia, associated with both said base and said cap, that may be selectively manipulated in a manner that indicated whether the container was used with a right breast or a left breast; said indicia comprising a first indicia that denotes "right" and second indicia that denotes "left"; the first and second indicia being positioned on said cap and an indicator being positioned on said base so that said base and said cap may be selectively rotated with respect to one another to associate said indicator with one of said first or second indicia and an axis extending perpendicularly through a central portion of the opening in said cap, positioned between a peripheral edge portion of said cap and an axis extending perpendicularly through a central portion of said cap.

6. The container of claim 5 wherein said indicia is comprised a first indicia that denotes "right" and a second indicia that denotes "left."

7. The container of claim 6 wherein the first and second indicia are positioned on said cap and an indicator is positioned on said base so that said base and said cap may be selectively rotated with respect to one another to associate said indicator with one of said first or second indicia.

8. The container of claim 7 wherein said indicator is provided in the form of a spout that extends outwardly from said base; said spout having an opening that is in open fluid communication with the open cavity of said base.

9. A container for receiving milk from a breast, the container comprising:
   a cup-shaped base, having at least one wall and a peripheral edge portion that define an open cavity;
   a cap that is shaped and sized to operatively engage the peripheral edge portion of said base in a manner that at least partially encloses said open cavity; said cap having an opening that is shaped and sized to accommodate at least a portion of a nipple on the breast; said cap and said base being operatively coupled with one another in a manner that permits selective rotational movement of said cap and said base with respect to one another;
   indicia, associated with both said base and said cap, that may be selectively manipulated in a manner that indicated whether the container was used with a right breast or a left breast; said indicia comprising a first indicia that denotes "right" and second indicia that denotes 'left"; the first and second indicia being positioned on said cap and an indicator being positioned on said base so that said base and said cap may be selectively rotated with respect to one another to associate said indicator with one of said first or second indicia and
   a reservoir adjacent said base; said reservoir having an inner chamber that is in open fluid communication with the open cavity of said base.

10. The container of claim 9 wherein an open neck member connects said reservoir with said base; said neck member having a cross-sectional height that is shorter than a cross-sectional height for said base or a cross-sectional height of said reservoir.

11. The container of claim 10 wherein said neck member is flexible so that said base and said reservoir may be selectively moved with respect to one another.

12. The container of claim 11 wherein said neck member is comprised of a resiliently deformable material.

13. The cover of claim 10 wherein said base and said neck member are shaped so that said base may be substantially disposed within a cup of a brassiere, while the brassiere is worn by an individual, and said neck member may be disposed between a peripheral edge portion of the bra to support said reservoir outside the brassiere cup in a manner that permits fluid to drain freely from said base into said reservoir.

14. The container of claim 13 wherein said reservoir is provided with a lower end portion that is shaped to permit the container to be positioned on said lower end portion and support said base above an operating surface.

15. The container of claim 9 wherein said indicator is provided in the form of a spout that extends outwardly from said base; said spout having an opening that is in open fluid communication with the open cavity of said base.

16. The container of claim 1 wherein the container is comprised of a material containing phosphors so that at least portions of the container will radiate visible light after said phosphors are energized.

* * * * *